United States Patent
De Vries et al.

(10) Patent No.: US 9,555,019 B2
(45) Date of Patent: Jan. 31, 2017

(54) GRANULATE CONTAINING CANNABINOID, METHOD FOR ITS MANUFACTURE AND ORAL DOSAGE UNIT COMPRISING SUCH GRANULATE

(71) Applicant: Echo Pharmaceuticals B.V., Weesp (NL)

(72) Inventors: Jan Albert De Vries, Zelhem (NL); Maria Vanesa Fernandez Cid, Haarlem (NL); Ana Maria Heredia Lopez, Amsterdam (NL)

(73) Assignee: Echo Pharmaceuticals B.V., Weesp (NL)

( * ) Notice: Subject to any disclaimer, the term of this patent is extended or adjusted under 35 U.S.C. 154(b) by 0 days.

(21) Appl. No.: 15/223,783

(22) Filed: Jul. 29, 2016

(65) Prior Publication Data

US 2016/0367522 A1    Dec. 22, 2016

Related U.S. Application Data

(62) Division of application No. 14/399,487, filed as application No. PCT/NL2013/050341 on May 3, 2013.

(30) Foreign Application Priority Data

May 7, 2012 (EP) .................................. 12167006

(51) Int. Cl.
  *A61K 31/05*   (2006.01)
  *A61K 31/352*  (2006.01)
  *A61K 9/48*    (2006.01)
  *A61K 9/20*    (2006.01)
  *A61K 9/00*    (2006.01)

(52) U.S. Cl.
  CPC ........... *A61K 31/352* (2013.01); *A61K 9/0053* (2013.01); *A61K 9/2013* (2013.01); *A61K 9/2018* (2013.01); *A61K 9/2095* (2013.01); *A61K 9/4858* (2013.01); *A61K 31/05* (2013.01)

(58) Field of Classification Search
  CPC ............... A23V 2002/00; A23V 2200/224; A23V 2250/5114; A23V 2250/616; A23V 2250/70; A23V 2250/5118; A23V 2250/628; A23V 2250/702; A23V 2250/708; A23V 2250/712; A23V 2250/61; A61K 31/352; A61K 2300/00
  See application file for complete search history.

(56) References Cited

U.S. PATENT DOCUMENTS

2010/0034888 A1* 2/2010 Pellikaan .......... A61K 9/1617
                                                    424/489

FOREIGN PATENT DOCUMENTS

| DE | 103 41 264 A1 | 3/2005 | |
| FR | WO02/064109 A2 * | 8/2002 | ............ A61K 9/006 |
| WO | WO-02/064109 A2 | 8/2002 | |
| WO | WO-2005/004848 A1 | 1/2005 | |
| WO | WO-2008/033024 A2 | 3/2008 | |

OTHER PUBLICATIONS

Heng, Paul Wan Sia et al., "Investigation of Melt Agglomeration Process with a Hydrophobic Binder in Combination with Sucrose Stearate," European Journal of Pharmaceutical Sciences, vol. 19, 2003, pp. 381-393.
International Preliminary Examination Report mailed May 16, 2014 in PCT/NL2013/050341.
International Search Report mailed Sep. 5, 2013 in PCT/NL2013/050341.

* cited by examiner

*Primary Examiner* — Audrea Buckley
(74) *Attorney, Agent, or Firm* — Foley & Lardner LLP; Sunit Talapatra

(57) ABSTRACT

The present invention relates to a granulate comprising granules made up of 40-99 wt. % of lactose particles and 1-60 wt. % of a binding component that holds together the lactose particles within the granules. Said granules have a mass weighted average diameter of 50-500 μm and said binding component is a solid dispersion or a solid solution of 10-75 wt. % of a cannabinoid in 25-80 wt. % of a lipophilic matrix. The lipophilic matrix contains at least 80 wt. % sucrose fatty acid mono-ester, the fatty acid residue being selected from $C_8$-$C_{18}$ fatty acids.
The aforementioned granulate can be processed into oral dosage units in the form of tablets for oral delivery.
The invention further provides a method for the manufacture of the granulate.

15 Claims, 2 Drawing Sheets

GRANULATE CONTAINING CANNABINOID, METHOD FOR ITS MANUFACTURE AND ORAL DOSAGE UNIT COMPRISING SUCH GRANULATE

CROSS REFERENCE TO RELATED APPLICATIONS

This application is a Divisional Application of U.S. application Ser. No. 14/399,487, filed Nov. 6, 2014, which is the National Phase of International Patent Application No. PCT/NL2013/050341, filed May 3, 2013, published as WO 2013/169101 A1, which claims priority to European Application No. 12167006.1 filed May 7, 2012. The contents of these applications are herein incorporated by reference in their entirety.

TECHNICAL FIELD OF THE INVENTION

The present invention relates to granulates containing lactose particles and a binding component comprising a cannabinoid and a sucrose fatty acid mono-ester. These granulates are particularly suited for use in dosage units that are intended for peroral administration. The invention also provides a method for the manufacture of the granulates.

BACKGROUND OF THE INVENTION

Biological availability of pharmaceutical substances taken perorally depends on the extent to which the pharmaceutically active substance is absorbed from the intestinal environment across the intestinal mucosa. Hydrophobic pharmaceutical substances are generally poorly absorbed from the intestinal environment, inter alia because of their poor solubility and/or dispersibility in water.

The biological availability of pharmaceutical substances taken perorally is furthermore greatly dependent on their susceptibility to the so-called first pass effect Substances absorbed from the intestine, before being distributed throughout the body, have to pass the liver first where they may be metabolized immediately. This first pass effect is dependent on the substance. In the case of cannabinoids, examples are known in which more than 90% of the ingested dose is removed from the blood stream during the first pass.

Hence, ingestion or peroral administration of cannabinoids generally results in poor bioavailability.

Accordingly, over the years much effort has been put in the development of pharmaceutical delivery systems for transmucosal administration, especially buccal and sublingual administration of cannabinoids.

For transmucosal administration, it is important that the substance is rapidly released from the delivery system into the aqueous environment covering the mucosal surface so that it can be absorbed across said mucosal tissue. Especially in case a pharmaceutically active substance is poorly water-soluble or water-dispersible, it is a major challenge to formulate a delivery system that will achieve fast release of the pharmaceutically active substance in the fluid surrounding the mucosa so as to enable effective absorption of the pharmaceutically active substance by the mucosal tissue.

WO 2008/033024 A2 describes dosage units for sublingual, buccal or oral administration of water-insoluble pharmaceutically active substances. Example 1 describes the preparation of a monophasic microgranulate comprising Δ-9-tetrahydrocannabinol, and sucrose monolaurate in a weight ratio of 1:15 using a dry granulation process. Example 3 of this patent application describes the manufacture of a tabletting powder for direct compression using 50 g of the microgranulate obtained from Example 1 and 17 g of other components including 5 g of lactose and the compression to 7 mm tablets with a total weight of 60 mg. This patent application does not describe peroral administration.

WO 02/064109 A2 describes a pharmaceutical formulation for use in administration of a lipophilic medicament via a mucosal surface, which formulation comprises at least one lipophilic medicament and at least one self emulsifying agent, wherein the formulation, upon hydration, forms an emulsion containing the lipophilic medicament which is capable of adhering to a mucosal surface and allowing controlled release of the medicament. Also described are pharmaceutical formulations in the form of a gel or a compressed tablet for administration of a lipophilic medicament via the sublingual and/or buccal mucosa, wherein the tablet or gel, upon contact with saliva, forms an emulsion containing the lipophilic medicament that adheres reversibly to the sublingual and/or buccal mucosa. Example 6 of the patent application describes the preparation of a tablet for buccal or sublingual administration by dissolving glyceryl monostearate, polysorbate 80, ascorbyl palmitate and α-tocopherol and THC in alcohol, spraying the alcoholic solution onto a powder mix consisting of lactose and soluble starch, evaporating the alcohol, dusting the resulting granulate with talc and compressing to a target tablet weight of 101 mg. WO 02/064109 A2 aims at absorption via the sublingual and/or buccal mucosa since it is stated that medicaments taken perorally, i.e. taken by ingestion, are subject to the so-called first pass effect which would considerably limit the biological availability of the pharmaceutical substance.

WO 2005/004848 A1 relates to solid dispersions comprising tacrolimus and solid surfactant having a hydrophile lipophile balance (HLB) value higher than or equal to about 7. Example 19 describes the preparation of the solid dispersion of tacrolimus. Tacrolimus (30 g) was dissolved in the mixture of ethanol (100 ml) and dichloromethane (50 ml). In the thus obtained solution, sucrose fatty acid ester (HLB=9, 90 g) was dispersed as the drug carrier. The solution was sprayed on lactose (300 g) that was fluidized in a fluid bed granulator, and then dried.

In spite of the attempts to develop suitable buccal or sublingual transmucosal delivery systems, peroral administration is still generally seen as a more convenient mode of administration.

It is therefore an object of the present invention to provide oral dosage units for peroral delivery of cannabinoid with improved bioavailability.

SUMMARY OF THE INVENTION

The inventors have developed a granulate comprising granules made of lactose particles held together by a binding component comprising a cannabinoid and a lipophilic matrix. This lipophilic matrix contains at least 80 wt. % of sucrose mono-ester of a $C_8$-$C_{18}$ fatty acid. Without wishing to be bound by any theory, it is hypothesized that the sucrose fatty acid mono-ester acts as a binder itself and enables the formation of a granulate with the cannabinoid.

The granulates of the present invention can be easily processed into oral dosage units in the form of tablets for peroral delivery. The present inventors have surprisingly found that peroral administration of the dosage units according to the present invention results, despite the first pass effect, in sufficient bioavailability of the cannabinoid.

Although the inventors do not wish to be bound by any particular theory, it is hypothesized that the use of lactose particles and the addition of sucrose fatty acid mono-ester to the granulates of the present invention, in the relative amounts given above, greatly enhances the water solubility and absorption of the cannabinoid across the intestines into the bloodstream.

DEFINITIONS

Figure 1:
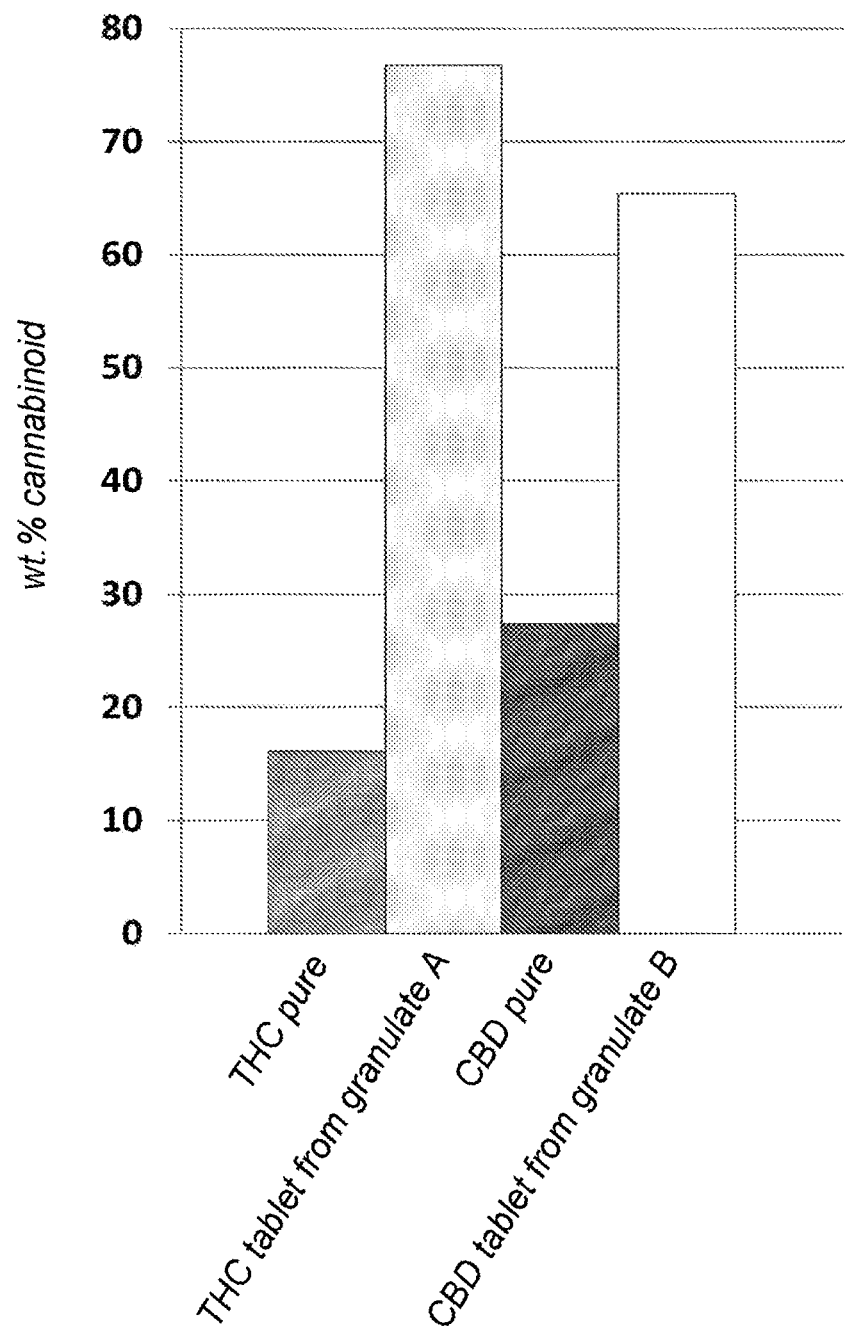
FIG. 1 depicts results from dissolution test of different cannabinoids formulated according to the present invention. The weight percentage (wt. % cannabinoid) refers to the weight of the cannabinoid found in the dissolution medium as compared to the total weight of the cannabinoid present in the tablet that is added to the dissolution medium.

The term 'granulate' as used herein refers to a particulate material that consists of small discrete particles, the so-called granules. A granule is an aggregation of component particles that is held together by physical forces. In a wet granule, these forces are due to the surface tension and due to capillary forces of a liquid binding component. These forces are also responsible for the initial agglomeration of the component particles.

The term 'granulation' in the context of the present invention is understood to be a process that converts a mixture of powders, the particles of which have poor cohesion, into aggregates capable of compaction. Unless indicated otherwise, the term granulation as used herein refers to the process of 'wet granulation'.

The term 'oral' or 'peroral' as used herein, unless indicated otherwise, refers to a mode of administration that involves ingestion of the dosage unit without significant residence lime in the oral cavity.

The term 'mass weighted average diameter' as used herein refers to the average diameter of particulate matter as measured by analytical sieve analysis (see for example H. G. Brittain, *Pharmaceutical Technology*, December 2002, pp 56-64). In this analytical method, with which the expert in the field of pharmaceutical drug formulations is familiar, sieves are stacked on top of each other in ascending degrees of coarseness, and the powder to be tested is placed on the top sieve. The nest of sieves is subjected to a standardized period of agitation, which causes the powder sample to distribute between the sieves. Subsequently, the weight percentage of powder retained in each sieve size range is determined. The 'mass weighted average diameter' is than obtained from a plot of the cumulative weight distribution versus sieve mesh size by determining the mesh size corresponding to 50 wt. % of total powder mass.

DETAILED DESCRIPTION OF THE INVENTION

A first aspect of the invention relates to a granulate comprising granules made up of 40-99 wt. % of lactose particles and 1-60 wt. % of a binding component that holds together the lactose particles within the granules, said granules having a mass weighted average diameter of 50-500 µm and said binding component being a solid dispersion or a solid solution of 10-75 wt. % of a cannabinoid in 25-80 wt. % of a lipophilic matrix, said lipophilic matrix containing at least 80 wt. % sucrose fatty acid mono-ester, the fatty acid residue being selected from $C_8$-$C_{18}$ fatty acids.

The granulates of the present invention are particularly suited for delivering hydrophobic cannabinoids that are poorly water-soluble or poorly dispersible in water. Typically, the solubility of these cannabinoids in demineralized water is less than 1 mg/ml at a temperature of 25° C., preferably less than 0.1 mg/ml at 25° C., more preferably less than 0.003 mg/ml at 25° C.

Cannabinoids, which are substituted meroterpenes, are the major active constituents of the plant *Cannabis sativa*. The most important natural cannabinoid is the psychoactive Δ9-tetrahydrocannabinol. The term 'cannabinoid' as used herein encompasses the following substances: Δ-8-tetrahydrocannabinol, Δ-9-tetrahydrocannabinol (THC), cannabidiol (CBD), olivetol, cannabinol (CBN), cannabigerol (CBG), cannabichromene (CBC), Tetrahydrocannabivarin (THCV), Δ9-Tetrahydrocannabinol-C4 (THC-C4), nabilone, Δ-9-tetrahydro cannabinolic acid (THC-A), Cannabichromenic acid (CBC-A), Cannabigerolic acid (CBG-A) as well as the prodrugs and pharmaceutically acceptable salts of these cannabinoids. Preferred cannabinoids that can be incorporated in the granulates according to the present invention are THC, CBD, and mixtures thereof, most preferably THC.

As explained herein before, the present granulate comprises lactose particles, and a binding component that holds together the lactose particles within the granules i.e. the granules are biphasic. The phase comprising lactose particles is hydrophilic in nature. The phase comprising the binding component comprises the cannabinoid and an amphiphilic sucrose fatty acid mono-ester and is thus hydrophobic/lipophilic in nature. The phase comprising the binding component can be a solid dispersion or a solid solution. A solid dispersion is a dispersion of one or more compound(s) in a carrier at solid state. The dispersed compounds can consist of individual molecule unities or of clusters such as in particles. A solid solution in the context of the present invention is a true mixture of compounds that is homogeneous at the molecular level.

In a preferred embodiment, the binding component is a solid dispersion, which contains dispersed particles comprising the cannabinoid, said particles having a volume weighted average diameter between 2 nm and 1 µm, more preferably of 2-500 nm, most preferably of 2-300 nm.

In a preferred embodiment, at least 80 wt. % of the granules constituting the granulate have a diameter in the range of 50-500 µm.

Furthermore, in a preferred embodiment, the granulate comprises granules containing 50-98 wt. % lactose particles and 2-50 wt. % of the binding component. In an even more preferred embodiment, the granules contain 60-95 wt. % lactose particles and 5-40 wt. % of the binding component.

Lactose has a water solubility of 18.9 g at 25° C. and 25.1 g at 40° C. per 100 g solution. This considerable aqueous solubility helps the granulates to disintegrate quickly in aqueous environments.

Lactose is a disaccharide of glucose and galactose. The glucose can be in either the α-pyranose form or the β-pyranose form, whereas the galactose can only have the β-pyranose form. Hence, lactose can take two different anomeric forms which are referred to as α-lactose and β-lactose. In a preferred embodiment, the lactose particles consist of from 50 to 100 wt. % of β-lactose, more preferably from 75 to 100 wt. %.

Without wishing to be bound by any particular theory it is hypothesized that the combination of the water-soluble lactose particles and the amphiphilic sucrose fatty acid mono-ester contributes to the absorption of the cannabinoid from the aqueous environment of the gastrointestinal tract through the lipophilic gut wall into the bloodstream.

(Spray-dried) lactose contains 8 hydroxyl groups that may be capable of reacting with functional groups on the cannabinoid, for example under the influence of moisture. In a preferred embodiment the lactose constituting the lactose particles is anhydrous lactose. Anhydrous lactose is lactose that is substantially free of (crystal) water. Anhydrous lactose is known to offer the best compactability of all grades of lactose, and it is well suited to direct compression applications.

The binding component comprises a cannabinoid in a lipophilic matrix, said lipophilic matrix containing at least 80 wt. % of sucrose fatty acid mono-ester, the fatty acid residue being selected from $C_8$-$C_{18}$ fatty acids. In an embodiment of the invention, the lipophilic matrix consists of sucrose fatty acid mono-ester.

The binding component may in addition to the cannabinoid and the sucrose fatty acid mono-ester suitably contain additional excipients such as antioxidants, preservatives, fat, wax, or further pharmaceutically active substances, et cetera. In a preferable embodiment, the cannabinoid and the sucrose fatty acid mono-ester together represent at least 60 wt. % of the binding component, more preferably at least 80 wt. %.

Non-limiting examples of antioxidants that can be employed in the binding component include α-tocopherol (vitamin E), ascorbic acid (vitamin C), ascorbyl palmitate (derivative of vitamin C), vitamin A, flavanoids, polyphenols, butylated hydroxy anisole, carotenes, ubiquinol (coenzyme Q10), and combinations thereof. In a preferred embodiment the antioxidant is ascorbic acid.

Sucrose fatty acid mono-esters are amphiphilic compounds, i.e. they comprise a hydrophilic and a lipophilic part. The balance between their hydrophilicity and lipophilicity can be expressed in the so-called HLB value. HLB-values can range from 0 to 20. Compounds with HLB values between 3 and 6 are lipophilic in nature and form water-in-oil (W/O) emulsions, while values of 8-18 indicate hydrophilic characteristics which is related to the formation of oil-in-water (O/W) emulsions. According to a preferred embodiment the sucrose fatty acid mono-ester is an oil-in-water (O/W) emulsifier. The HLB-value of the sucrose fatty acid mono-ester depends on the type of fatty acid residues. According to a particularly, preferred embodiment, the sucrose fatty acid mono-ester has an HLB-value of 8-18.

Commercially available sucrose fatty acid mono-esters usually contain small amounts of sucrose di-esters. The present granulate preferably comprises less than 10 wt. % of sucrose di-esters calculated by weight of the sucrose fatty acid mono-ester, more preferably less than 5 wt. % of sucrose di-esters calculated by weight of the sucrose fatty acid mono-ester.

In a preferred embodiment, the fatty acid residue of the sucrose fatty acid mono-ester is a saturated $C_{10}$-$C_{18}$ fatty acid.

In an even more preferred embodiment, the fatty acid residue of the sucrose fatty acid mono-ester is selected from lauric, palmitic or stearic acid.

In a most preferred embodiment, the sucrose fatty acid mono-ester is sucrose mono-laurate (SML).

Another aspect of the invention relates to oral dosage units containing between 10 wt. % and 98.8 wt % of the granulate according to any of the foregoing. Such dosage units may typically take the form of compressed tablets, capsules containing the granulate, powders, pills, etc. Tablets obtained by direct compression of the granulate of the invention are particularly preferred.

In a preferred embodiment the oral dosage unit comprises at least 1 wt. % of cannabinoids. Even more preferably, the present dosage unit contains 1-8 wt. % of cannabinoids, most preferably 1-6 wt. % of cannabinoids. Preferably, the present dosage unit contains THC, CBD or mixtures thereof.

The oral dosage units according to the invention may further include one or more excipients chosen from the group consisting of coloring agents, flavoring or taste masking agents, muco-adhesive agents, diluents, binders, lubricants, additional disintegrants, stabilizers, surfactants, glidants, plasticizers, preservatives and sweeteners.

Suitable muco-adhesive agents that can be added to the oral dosage units are chosen from the group consisting of carbomers, cellulose derivatives, plant lectin, dextrin, hypromellose, chitosan, polyethylene oxide, alginate and combinations thereof. In a preferred embodiment the oral dosage units comprise up to 3 wt. % of muco-adhesive agents.

The additional disintegrants are advantageously chosen from the group consisting of lactose, anhydrous lactose, crospovidone, croscarmellose sodium, sodium starch glycolate, hydroxypropyl cellulose, polacrilin potassium, pregelatinized starch, microcrystalline cellulose and combinations thereof. In a preferred embodiment the oral dosage units comprise up to 25 wt. % of additional disintegrants.

The dosage unit of the present invention may suitably take the shape of a compressed tablet. Such a tablet may suitably comprise two or more layers of different composition, for example a core obtained by direct compression of the granulate encased in a coating. The dosage units of the present inventions are conveniently produced in a tabletting machine. In order to enable easy removal of the tablets from the moulds, the dosage unit typically contains 0.1-10% of a lubricant or gliding agent. Preferably, the lubricant or gliding agent is selected from the group consisting of talc, sodium stearyl fumarate, magnesium stearate, calcium stearate, hydrogenated castor oil, hydrogenated soybean oil, polyethylene glycol, starches, anhydrous colloidal silica and combinations thereof. In a preferred embodiment the oral dosage units comprise 1 wt. % of lubricant.

According to a preferred embodiment, the dosage unit of the present invention comprises a combination of silica, disintegration agent, muco-adhesive agent and lubricant, said combination representing at most 38 wt. %, preferably at most 30 wt. % of the hydrophilic matrix.

Advantageously, the dosage unit exhibits a certain level of porosity in order to allow easy water access. Typically, the dosage units of the present invention exhibit a porosity of 1-50%, preferably of 2-15%.

Another aspect of the invention relates to oral dosage units according to any of the foregoing for use in therapeutic of prophylactic treatments, said use comprising oral (peroral) administration of the dosage unit.

The pharmaceutical dosage units of the present invention are advantageously employed in the therapeutic or prophylactic treatments of mammals, preferably of humans.

Cannabinoid containing dosage units according to this inventions are particularly suitable for use in treatment of psychiatric disorders, behavioural disorders, schizophrenia, anxiety, epilepsy, movement disorders, eating disorders, Alzheimer, stroke, multiple sclerosis, spinal cord injury, peripheral neuropathy, neurogenic pain, nociceptive pain or nausea. Furthermore, said dosage units may advantageously be used as a sedative or a sedative-enhancer in combined treatments.

Another aspect of the invention relates to a method of preparing a granulate as described herein before, said method comprising the steps of:
  providing a lactose powder having a mass weighted average diameter of 32-250 um, preferably of 45-250 μm;
  granulating the lactose powder by combining it with a granulation liquid, said granulation liquid comprising a solution of a cannabinoid and sucrose fatty acid mono-ester in an organic solvent, preferably $C_1$-$C_3$ alcohol, the fatty acid residue being selected from $C_8$-$C_{18}$ fatty acids; and
  removing the organic solvent by evaporation.

As is already explained in the foregoing, the granulation method according to the present invention includes wet granulation. In wet granulation a binder solution is prepared which is slowly added to a powder under continuous agitation of the mixture. Addition of the binder solution causes aggregation of the powder particles. Following the aggregation step, the solvent of the binder solution is removed using a drying step. As is known to those skilled in the art, the rate of adding the binder solution to the powder, the ratio of binder-solution to powder and the degree of agitation of the wet mass all affect the final particle size distribution of the granules.

In a preferred embodiment, the temperature of the granulation liquid is between 15° C. and 50° C. when it is combined with the lactose powder.

All components that are to constitute the binding component of the granulate are dissolved in an organic solvent, preferable a $C_1$-$C_3$ alcohol. This solution is referred to as the granulation fluid. The organic solvent is chosen such that all components to be dissolved have a certain minimum solubility at the process temperature. Those skilled in the art of pharmaceutical drug formulations are familiar with such routine optimizations.

In a preferred embodiment, the $C_1$-$C_3$ alcohol is chosen from the group consisting of methanol, ethanol, n-propanol, isopropyl alcohol and combinations thereof. In a particularly preferred embodiment, the $C_1$-$C_3$ alcohol is ethanol, even more preferably anhydrous ethanol.

Evaporation of the $C_1$-$C_3$ alcohol can be accomplished by any means known in the art. Non-limiting examples that can be suitably applied in the present method are vacuum distillation and conventional distillation by heating the granulate, causing evaporation of the alcohol, and by removing the vapor from the system using a condenser, and combinations thereof. In a preferred embodiment, vacuum distillation is applied. In a more preferred embodiment, the vacuum distillation is applied at a temperature of between 20° C. and 70° C., even more preferably at a temperature of between 35° C. and 55° C.

In another preferred embodiment, a method is provided according to any of the foregoing, wherein the granulation liquid has the following composition:
  40-55 wt. % $C_1$-$C_3$ alcohol;
  15-20 wt. % cannabinoid;
  30-40 wt. % sugar fatty acid mono-ester.

The following examples are meant to further illustrate the invention and some of its preferred embodiments without intending to limit its scope.

EXAMPLES

Example 1

Preparation of Granulate A

Components used for the preparation of granulate A are described in Table 1.

TABLE 1

| Component | wt. % |
| --- | --- |
| THC | 3.0 |
| SML | 6.0 |
| Ascorbic acid | 0.3 |
| Lactose (direct compression grade*) | 90.7 |

*mass weighted average diameter < 250 μm

Granulate A is prepared via a wet-granulation method. A mixture of THC, SML and ascorbic acid (AA) is dissolved in ethanol. The resulting solution is added to the lactose placed in the granulation vessel. The ethanol is evaporated and the resulting granulate is sieved. The granulate with a mass weighted average diameter of 300 μm is ready for further processing into tablets or for filling into (hard) gelatin capsules. The binding component of the granulate consists of a solid solution of THC, SML and ascorbic acid.

Example 2

Preparation of Granulate B

Components used for the preparation of granulate B are described in Table 2.

TABLE 2

| Component | wt. % |
| --- | --- |
| CBD | 8.0 |
| SML | 16.0 |
| Ascorbic acid | 0.8 |
| Lactose (spray-dried lactose*) | 75.2 |

*mass weighted average diameter < 200 μm

Granulate B with an mass weighted average diameter of 300 μm is prepared as described in example 1.

Example 3

Preparation of Oral Dosage Forms

Granulate A and B were blended with excipients and direct compressed into oral tablets. The components used for tablet preparation are given in Table 3.

TABLE 3

| Component | wt. % |
|---|---|
| Granulate | 75 |
| Lactose (direct compression grade*) | 23.8 |
| Magnesium Stearate | 1 |
| Silicon dioxide | 0.2 |

*mass weighted average diameter < 250 μm

Dissolution tests with the tablets according to the method described in the European Pharmacopeia (Ph. Eur. 2.9.3) for oral tablets were performed to compare the effect of the invention herein described on the rate of dissolution of the cannabinoid. The rate of dissolution of the pure cannabinoid was also measured according to the same method for comparison. The dissolution media consisted of a solution of 1 wt. % SDS in water and a pH of 7 readjusted with dilute HCl. During the experiments the temperature of the dissolution media was maintained between 36 and 41° C. under stirring. After dropping the tablet in the dissolution media, samples were taken at various time intervals with the use of a disposable syringe. The samples were filtered immediately over a syringe filter into a HPLC vial and analyzed by HPLC.

FIG. 1 depicts results from dissolution test of different cannabinoids formulated according to the present invention. The weight percentage (wt. % cannabinoid) refers to the weight of the cannabinoid found in the dissolution medium as compared to the total weight of the cannabinoid present in the tablet that is added to the dissolution medium.

The results demonstrate the favourable effect of the present invention on the rate of dissolution of cannabinoid in aqueous media.

Comparative Example A

Tablets prepared from granulate A as described in example 3 were compared with tablets prepared according to example 6 in patent WO 02/064109 A2 via a dissolution test as described in example 3.

TABLE 4 composition of comparative example A

| Components | wt. % |
|---|---|
| Ascorbic Acid | 0.1 |
| Tocopherol | 0.2 |
| Glyceryl Monostearate (GMS) | 5.0 |
| Tween 80 | 0.5 |
| THC | 5.0 |
| Starch | 10.0 |
| Lactose (direct compression grade*) | 79.2 |

*mass weighted average diameter < 250 μm

Figure 2:
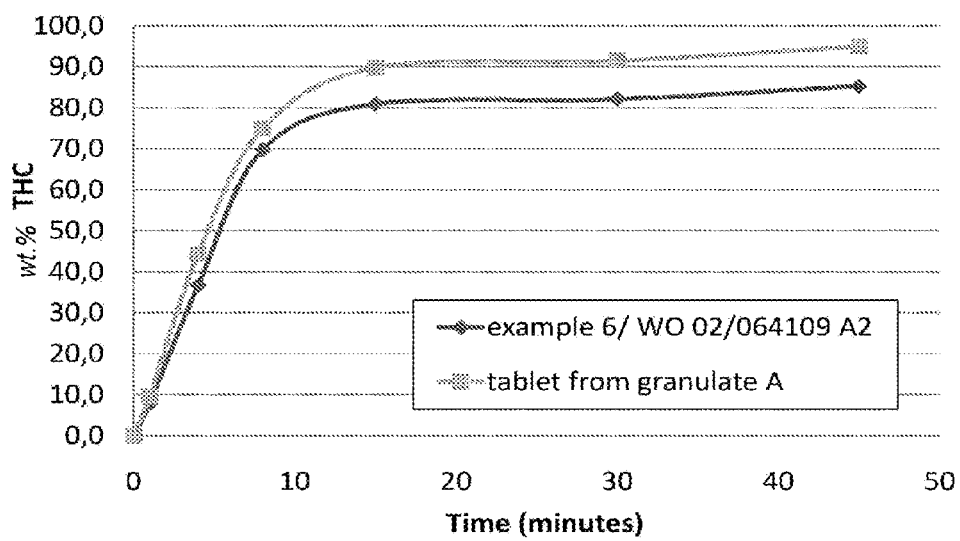
FIG. 2 shows dissolution results of THC from tablets prepared as in example 6 of WO 02/064109 A2 and from tablets prepared as in example 3 from granulate A. The weight percentage (wt. % THC) refers to the weight of the THC found in the dissolution medium as compared to the total weight of the THC present in the tablet that is added to the dissolution medium.

In FIG. 2, dissolution results of THC from tablets prepared as in example 6 of WO 02/064109 A2 and from tablets prepared as in example 3 from granulate A are compared. The weight percentage (wt. % THC) refers to the weight of the THC found in the dissolution medium as compared to the total weight of the THC present in the tablet that is added to the dissolution medium.

Even with the use of more than one amphiphilic compound and a disintegrant in the formulation of example 6 of WO 02/064109 A2, the dissolution rate of the THC is less than when THC is formulated according to example 3 of this patent.

Comparative Example B

Tablets were prepared as in example 4 with the only difference that the amphiphilic compound sucrose fatty ester (SML) was substituted by glyceryl monostearate (GMS). The dissolution test as described in example 5 was performed with these tablets and compared with those tablets prepared from granulate A and described in example 4.

Figure 3:
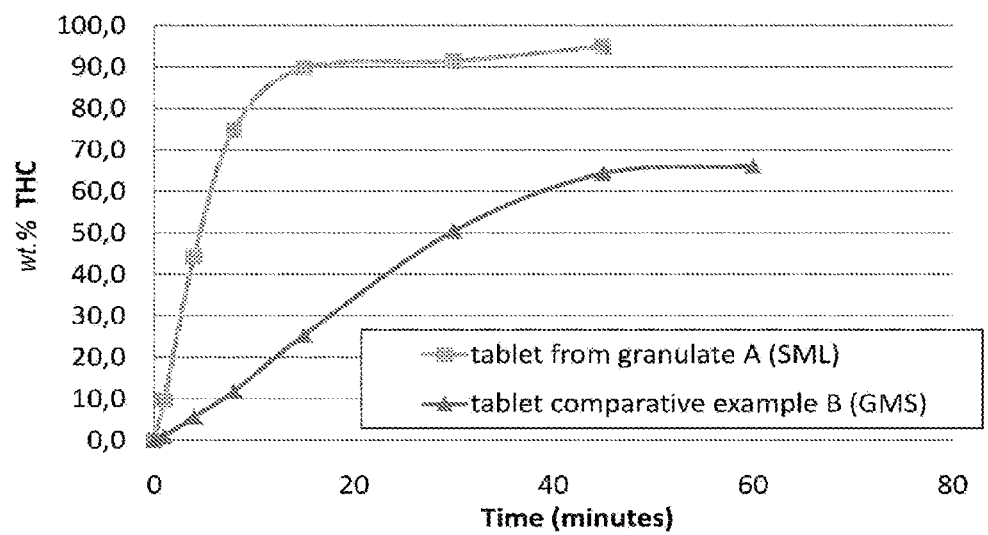
FIG. 3 shows the effects of sucrose fatty acid mono-ester (SML) and glyceryl monostearate (GMS) on THC dissolution. The weight percentage (wt. % THC) refers to the weight of the THC found in the dissolution medium as compared to the total weight of the THC present in the tablet that is added to the dissolution medium.

In FIG. 3, the effects of sucrose fatty acid mono-ester (SML) and glyceryl monostearate (GMS) on THC dissolution are compared. The weight percentage (wt. % THC) refers to the weight of the THC found in the dissolution medium as compared to the total weight of the THC present in the tablet that is added to the dissolution medium.

Tablets containing GMS in their formulation do not even comply with the Ph. Eur. specification for oral dosage forms (75% of the API must be released within 45 min). After 60 min not even 70% of all the THC has been released in the dissolution media, while with tablets from granulate A 90% of the THC release was achieved within 15 min.

The invention claimed is:

1. A method of preparing a granulate having a mass weighted average diameter of 50-500 μm, comprising:
   (a) providing a lactose powder having a mass weighted average diameter of 32-250 μm;
   (b) granulating the lactose powder by combining the powder with a granulation liquid comprising a solution of 10-75 wt. % of cannabinoid with sucrose fatty acid mono-ester having a C8-C18 fatty acid residue in a C1-C3 alcohol organic solvent; and
   (c) removing the organic solvent by evaporation,
   wherein the granules comprise 40-99 wt. % lactose.

2. The method according to claim 1, wherein the organic solvent is C1-C3 alcohol.

3. The method according to claim 2, wherein the alcohol is selected from the group consisting of methanol, ethanol, n-propanol and isopropyl alcohol.

4. The method according to claim 3, wherein the alcohol is ethanol.

5. The method according to claim 1, wherein the granulation liquid has the following composition:
   (a) 40-55 wt. % C1-C3 alcohol;
   (b) 20-75 wt. % of the cannabinoid; and
   (c) 30-40 wt. % of the sucrose fatty acid mono-ester.

6. The method according to claim 1, wherein the combination is at a temperature between 15° C. and 50° C.

7. The method according to claim 1, wherein the granules comprise 60-95 wt. % of lactose particles.

8. The method according to claim 1, wherein the fatty acid residue is a saturated C10-C18 fatty acid.

9. The method according to claim 1, wherein the sucrose fatty acid mono-ester is sucrose monolaurate.

10. The method according to claim 1, wherein the cannabinoid is selected from the group consisting of Δ-8-tetrahydrocannabinol, Δ-9-tetrahydrocannabinol (THC), cannabidiol (CBD), olivetol, cannabinol (CBN), cannabigerol (CBG), cannabichromene (CBC), Tetrahydrocannabivarin (THCV), Δ9-Tetrahydrocannabinol-C4 (THC-C4), nabilone, Δ-9-tetrahydro cannabinolic acid (THC-A), Cannabichromenic acid (CBC-A), Cannabigerolic acid (CBG-A).

11. The method according to claim 1, wherein the removing is by vacuum distillation or conventional distillation.

12. A method of preparing a tablet or compressed capsule dosage unit comprising:
   (a) providing a lactose powder having a mass weighted average diameter of 32-250 μm;

(b) granulating the lactose powder by combining the powder with a granulation liquid comprising a solution of a cannabinoid and sucrose fatty acid mono-ester in an organic solvent;
(c) removing the organic solvent by evaporation to obtain granules comprising 40-99 wt. % lactose; and
(d) compressing the granules with one or more pharmaceutically acceptable excipients to form a tablet or compressed capsule.

13. The method according to claim 12, wherein the excipients are selected from the group consisting of coloring agents, flavoring or taste masking agents, muco-adhesive agents, diluents, binders, lubricants, disintegrants, stabilizers, surfactants, glidants, plasticizers, preservatives and sweeteners.

14. The method according to claim 13, wherein the muco-adhesive agents are selected from the group consisting of carbomers, cellulose derivatives, plant lectin, dextrin, hypromellose, chitosan, polyethylene oxide, alginate and combinations thereof.

15. The method according to claim 13, wherein the disintegrants are selected from the group consisting of lactose, anhydrous lactose, crospovidone, croscarmellose sodium, sodium starch glycolate, hydroxypropyl cellulose, polacrilin potassium, pregelatinized starch, microcrystalline cellulose and combinations thereof.

* * * * *